(12) United States Patent
Vozhdayev (10) Patent No.: US 9,315,767 B1
(45) Date of Patent: Apr. 19, 2016

(54) PHOTO-BIOREACTOR FOR MASS PRODUCTION OF PHOTOSYNTHETIC ORGANISMS

(71) Applicant: Georgiy V. Vozhdayev, New Hope, MN (US)

(72) Inventor: Georgiy V. Vozhdayev, New Hope, MN (US)

( * ) Notice: Subject to any disclaimer, the term of this patent is extended or adjusted under 35 U.S.C. 154(b) by 221 days.

(21) Appl. No.: 13/828,324

(22) Filed: Mar. 14, 2013

Related U.S. Application Data (60) Provisional application No. 61/612,665, filed on Mar. 19, 2012.

(51) Int. Cl.
  *C12M 1/00* (2006.01)
(52) U.S. Cl.
  CPC .................................. *C12M 21/02* (2013.01)
(58) Field of Classification Search
  CPC .............................. C12M 21/02; B01D 21/24
  See application file for complete search history.

(56) References Cited

U.S. PATENT DOCUMENTS

| | | | |
|---|---|---|---|
| 7,997,025 B1* | 8/2011 | Masse | 47/1.4 |
| 8,809,037 B2* | 8/2014 | Haley et al. | 435/262.5 |
| 2002/0025547 A1* | 2/2002 | Rao | 435/40.5 |
| 2005/0260553 A1* | 11/2005 | Berzin | 435/3 |
| 2010/0255458 A1* | 10/2010 | Kinkaid | 435/3 |

OTHER PUBLICATIONS

Varma et al., Effect of sparger design on hydrodynamics of a gas recirculation anaerobic bioreactor, Dec. 15 2007, Biotechnology and Bioengineering, vol. 98, No. 6, p. 1146-1160.*

* cited by examiner

*Primary Examiner* — Lyle Alexander
*Assistant Examiner* — Holly Mull
(74) *Attorney, Agent, or Firm* — Mitchell A. Rossman; Terra Nova Patent Law, PLLC (57) ABSTRACT

The apparatus herein relates to the large-scale production of photosynthetic microorganisms, especially algae. More particularly it relates to control of large size aqueous photosynthetic bioreactor systems to obtain such products from many microbial strains, which have heretofore only been cultured in laboratory environments in small containers.

17 Claims, 12 Drawing Sheets

PHOTO-BIOREACTOR FOR MASS PRODUCTION OF PHOTOSYNTHETIC ORGANISMS

RELATED APPLICATION

The present application claims priority to U.S. Provisional Application No. 61/612,665 entitled PHOTO-BIOREACTOR FOR MASS PRODUCTION OF PHOTOSYNTHETIC ORGANISMS and filed Mar. 19, 2012, which is hereby incorporated herein in its entirety by reference.

FIELD OF THE INVENTION

The present invention is generally directed to a photo-bioreactor system for growing photosynthetic organisms. Specifically, the present invention is directed to a large scale photo-bioreactor system for producing biomass harvested from photosynthetic organism.

BACKGROUND OF THE INVENTION

As there begins to be an increased need for the development of renewable energy sources, the large scale production of algal bio-mass as means to produce a transportation fuel is becoming a highly sought after solution. Thus numerous ventures around the world have been organized to solve this problem. However, growing mass amounts of algae cheaply is difficult, and there are many obstacles that have to be overcome, with one of the major ones being frequent contamination events.

Thus the need to design a photo-bioreactor, which can grow a robust axenic culture, has become very apparent. When designing an effective solution, one also has to consider the many other contributing factors, such as energy balance, environmental impact, overall production rates, ease of harvest, capital expense, operating expense and, of course, sterility. An important factor for anyone attempting to develop a renewable fuel is keeping the overall energy balance of the production system positive, while allowing the system to function optimally. A major energy sink for most photo-bioreactor systems is the need for a cooling system. Maintaining an optimum temperature range (25° C.-39° C.) is crucial for the micro-organisms survival. Another factor that affects the energy balance of the system is the need for efficient $CO_2$ uptake. Being that $CO_2$ is an essential input to the production of autotrophic organisms it becomes an expensive commodity to waste if it's not over 90 percent utilized within the reactor.

SUMMARY OF THE INVENTION

A photo-bioreactor system, according to an embodiment of the present invention, comprises piping, valve work, control instrumentation, the novel growth chamber and accompanying components, all which contribute to optimal large scale production of photosynthetic micro-organisms, especially algae and cyanobacteria. The growth chamber, of pyramid geometry in this example embodiment, allows for optimum photon absorption by the community of microbes residing within the chamber, while maximizing total volume per given area. The growth chamber, being the primary assembly, can be made of transparent plastic, which encapsulates a volume of water, microbial culture, and necessary nutrient to produce bio-mass via photosynthesis. A support structure gives the photo-bioreactor its unique pyramid geometry, while allowing for sunlight to penetrate into the reactor.

In this example embodiment, the closed system photo-bioreactor can be capable of growing volumes as great as 167,000 L per reactor and greater, within a footprint of about 11.5 feet×200 feet or more. According to an embodiment of the present invention, the sixteen reactors can cover an area of approximately 1 sq. acre, as seen in FIG. 2, and allow for the controlled production of up to 2.5 million liters of microbial culture per acre.

Assuming a conservative rate of oil production of about 0.033-0.053 grams/liter/day, a rate that is easily produced by an algal species in autotrophic growth, an acre of land could therefore produce up to about 42,000 L of bio-diesel per year, and an additional 84,000 kilograms of de-wetted carbohydrates and proteins per year. These three main products can be accompanied by myriad of other high value products such as Polyunsaturated Fatty Acids (PUFAs), such as Omega-3s, which are essential for good health, plastic resins such as PHA and PHB, beta-carotene, as well as other chemical and pharmaceutical compounds. In addition, there is still substantial room for improvement of yields through optimization, as the previous numbers represent only examples of attained production yields.

The inventive concept described herein relies on the nature of certain species to flocculate, and settle out of solution, along the bottom surface of the growth chamber. A mechanism enables the harvest apparatus to roll back and forth along the floor of the growth chamber and collect the settled biomass. Suction created by the harvest pump is transferred through the manifold found along the length of the apparatus, and down along the floor of the harvest chamber. Two guide cables found on either side of the apparatus, guide the harvest apparatus along the length of the photo-bioreactor. As it comes in contact with the opposing wall of the reactor, a switch mechanism can be employed to reverse direction of motion of the apparatus and cause it to move in the opposite direction.

In another example embodiment, a flocculent can be utilized to induce settling for microbial strains that are more resistant to flocculation and settling.

Thus, the attributes that make this a unique apparatus are the following: Firstly, the pyramid shape of the reactor allows for greater penetration of photons into the growth chamber. The unique geometry of the reactor in combination with the placement of the air sparger system sub-assembly provides greater turbulence in the photo-bioreactor, and enables the reactor to grow a larger volume per given square meter than a point source mixing technique. The disclosed closed photo-bioreactor system could be capable of efficiently growing enormous volumes of culture at great concentrations while preserving valuable resources such as water.

The unique geometry of the example reactor in combination with the unique placement of the air sparger system sub-assembly also helps prevent the accumulation of bio-film along the inner surface walls of the photo-bioreactor, therefore allowing for maximum light penetration, and hence for optimum productivity via photosynthesis.

The filtration system, on the intake and exhaust sides of the photo-bioreactor system as seen in FIG. 1, helps to ensure sterility of the photo-bioreactor. Having an exhaust filter in place as a method of deterring contamination is a unique practice, and is an effective method in preventing contamination in the event of system pressure loss.

The return CO2 line, in combination with the method of diffusing CO2, improves the efficient use of CO2, and prevents waste CO2 from being lost into the atmosphere. This aspect overcomes a major obstacle that is important in achieving a photosynthetic system for production of renewable energy.

The nutrient delivery method, as well as construction technique are very unique to closed photo-bioreactor systems, and allow for even distribution of nutrient throughout the growth chamber, and promote even growth throughout the reactor.

The unique harvest apparatus design, is unlike any other device utilized in algal cultivation, and in combination with the novel growth chamber design, allows for very efficient harvest of biomass, which not only saves the algae growth operation hours in harvest time, but also drastically reduces operating expenses.

Lastly, the sheer volume of the culture within the reactor in combination with the air system, make a cooling system unnecessary, thus eliminating a large energy expense.

Therefore, the unique combination of sub-assemblies in conjunction with operation regime and novel photo-bioreactor geometry as described above, allow for a new method of large-scale algal cultivation.

A photo-bioreactor system for growing photosynthetic organisms to produce biomass, according to an embodiment of the present invention, can comprise a tubular growth chamber, a movable harvest manifold and a harvest pump for drawing a vacuum through the harvest manifold. The tubular growth chamber further comprises a plurality of elongated transparent panels arranged edgewise such that the tubular growth chamber comprises a generally flat bottom and at least two angled sides intersecting an apex and two end panels affixed to the ends of the plurality of elongated transparent panels to enclose the tubular growth chamber. In certain aspects, at least one of the end panels comprises at least one flanged component port for receiving sampling instrumentation for evaluating conditions within the tubular growth chamber. In certain embodiments, a support structure comprising a plurality of intersecting beams that can be overlaid on top of the tubular growth chamber to support the elongated panels. In certain aspects, a steel mesh or cage can be positioned in the gaps between the intersecting beams to reinforce and protect the transparent panels while not obstructing light passing between the beams. The tubular growth chamber can receive water, microbial cultures of photosynthetic organisms and nutrient solutions.

The harvest manifold is movable along the flat bottom of the tubular growth chamber and can comprise a plurality of hollow fingers through which a vacuum can be drawn by the vacuum pump to draw biomass settled on the flat bottom of the tubular grow chamber into the harvest manifold for collection. In certain aspects, the harvest manifold can further comprise at least one motor driven wheel engagable to the flat bottom to move the harvest manifold along the flat bottom of the tubular bioreactor. In this configuration, the tubular growth chamber can further comprise at least one guide wire extending between the end panels, wherein the harvest manifold further comprises a flanged fitting slidingly engagable to the guide wire to maintain the harvest manifold in a generally parallel orientation to the end panels as the harvest manifold is moving along the flat bottom.

In certain aspects, the photo-bioreactor system can further comprise at least one nutrient delivery tube extending along the apex of the tubular growth chamber and further comprising a plurality of perforations along the delivery tube for dispensing nutrients at the apex of the tubular growth chamber. The positioning of the nutrient delivery tube proximate the apex of the tubular growth chamber ensures that the delivered nutrients are evenly dispersed throughout the tubular growth chamber.

In certain embodiments, the photo-bioreactor system can further comprise at least one air sprager extending along the intersection of one of the sides and the bottom, wherein the air sprager comprises a plurality of perforations for expelling air into the tubular bioreactor from the air sprager. The perforations in the air sparger are oriented to direct the expelled air against the angled sides of the tubular bioreactor such that the air runs up the sides of the tubular bioreactor to dislodge biomass adhered to the sides. The air flow along the sides of the tubular bioreactor also serves to cool the bioreactor without the aid of separate cooling system.

In certain embodiments, the photo-bioreactor system can further comprise an exhaust assembly operably linked to the tubular bioreactor proximate the apex for receiving exhaust gas from the tubular bioreactor and comprising a selectable filter assembly. The selectable filter assembly can redirect the exhaust gas into the bioreactor if carbon dioxide is detected in the exhaust gas and venting the exhaust gas to atmosphere if no carbon dioxide is detected. In certain aspects, the exhaust assembly can further comprise a chimney component extending from the apex increasing headspace within the tubular bioreactor. The chimney component comprises an upper portion on which condensation can form and the chimney component comprises a vapor collection port, wherein the upper portion of the chimney component is angled to direct condensate into the vapor collection port.

A method of producing biomass from photosynthetic microorganisms, according to an embodiment of the present invention, can comprise providing a tubular growth chamber comprising a plurality of end panels and a plurality of elongated transparent panels arranged edgewise to define a generally flat bottom and at least two angled sides intersecting an apex. The method can further comprise filling the tubular growth chamber with a volume of water, at least one microbial culture of photosynthetic organisms and a nutrient solution, wherein the transparent panels allow entry of light to enter the tubular growth chamber to initiate microbial growth of the photosynthetic organisms. After growth of microbial culture, the method can also comprise moving a harvest manifold along the flat bottom of the tubular reactor and comprising a plurality of hollow fingers. Finally, the method can comprise drawing a vacuum through the hollow fingers to draw biomass settled on the flat bottom of the tubular grow chamber into the harvest manifold for collection.

In certain embodiments, the method can also comprise positioning at least one nutrient delivery tube along the apex of the tubular growth chamber, wherein the nutrient delivery tube comprises a plurality of perforations and dispensing a nutrient solution through the perforations of the nutrient delivery tube to evenly distribute the nutrient solution throughout the tubular bioreactor. Similarly, the method can also comprise positioning at least one air supply along the intersection of the angled sides and flat bottom of the tubular growth chamber, wherein the air sprager comprises a plurality of perforations and directing an air stream through the perforations in the air sprager such that the air stream runs up the sides of the tubular bioreactor to dislodge biomass adhered to the sides.

In certain embodiments, the method can further comprise sampling the carbon dioxide in the tubular bioreactor through a flanged port in the end panels of the tubular bioreactor and increasing air delivered to the bioreactor if the carbon dioxide falls beneath a predetermined threshold.

In certain embodiments, the method can further comprise linking an exhaust assembly to the apex of the tubular bioreactor, wherein the exhaust assembly further comprising a selectable filter assembly. The method can also comprise receiving a quantity of exhaust gas from the tubular bioreactor and returning the exhaust gas to the tubular bioreactor if the selectable filter assembly detects carbon dioxide in the exhaust gas. Similarly, the method can also comprise affixing a chimney to the apex of the tubular bioreactor to increase headspace within the tubular reactor, the chimney comprising an upper portion angled toward a vapor collection port and collecting condensation on the upper portion, wherein the angled upper portion directs the condensation toward the vapor collection port.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Figure 1:
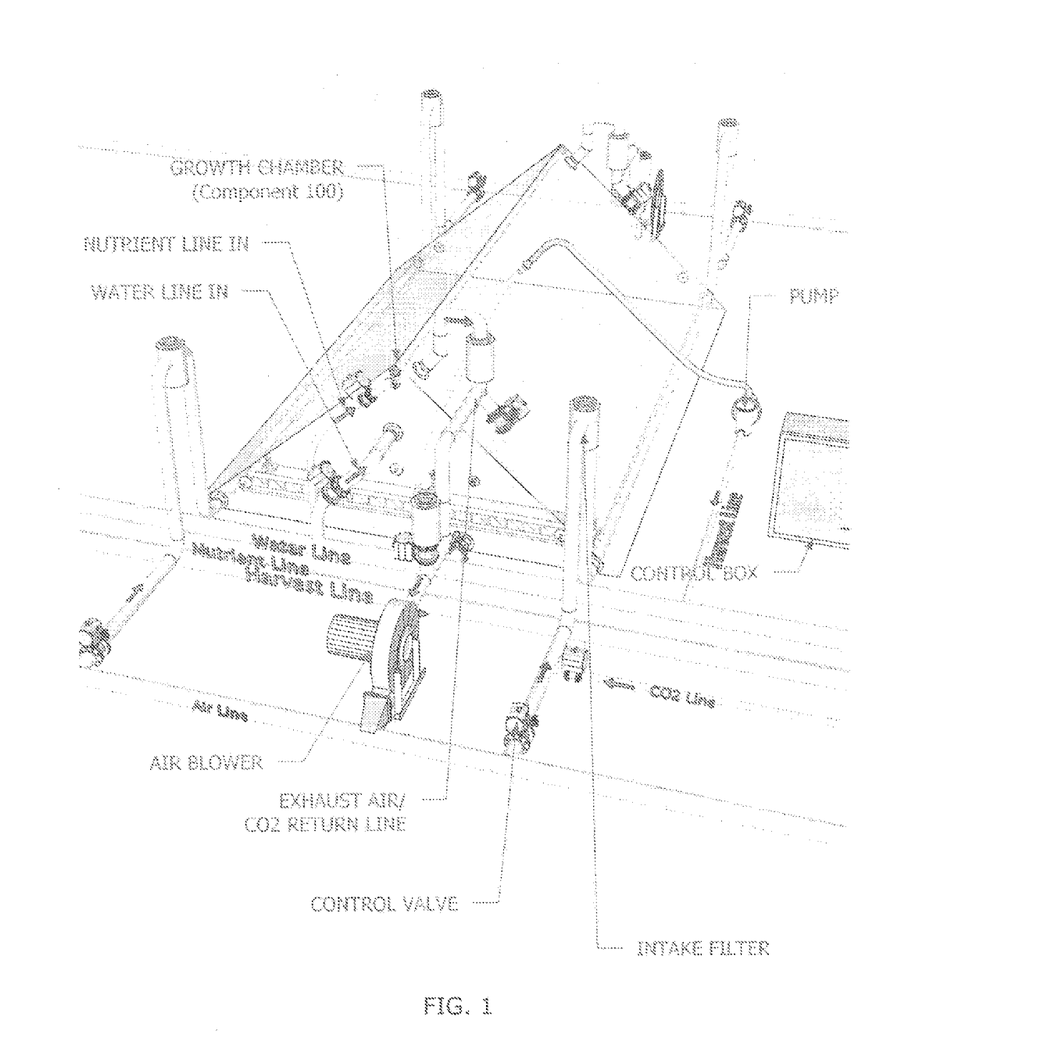
FIG. 1 shows an overall view of how a photo-bioreactor fits in with its operating system according to an embodiment of the present invention.
Figure 2:
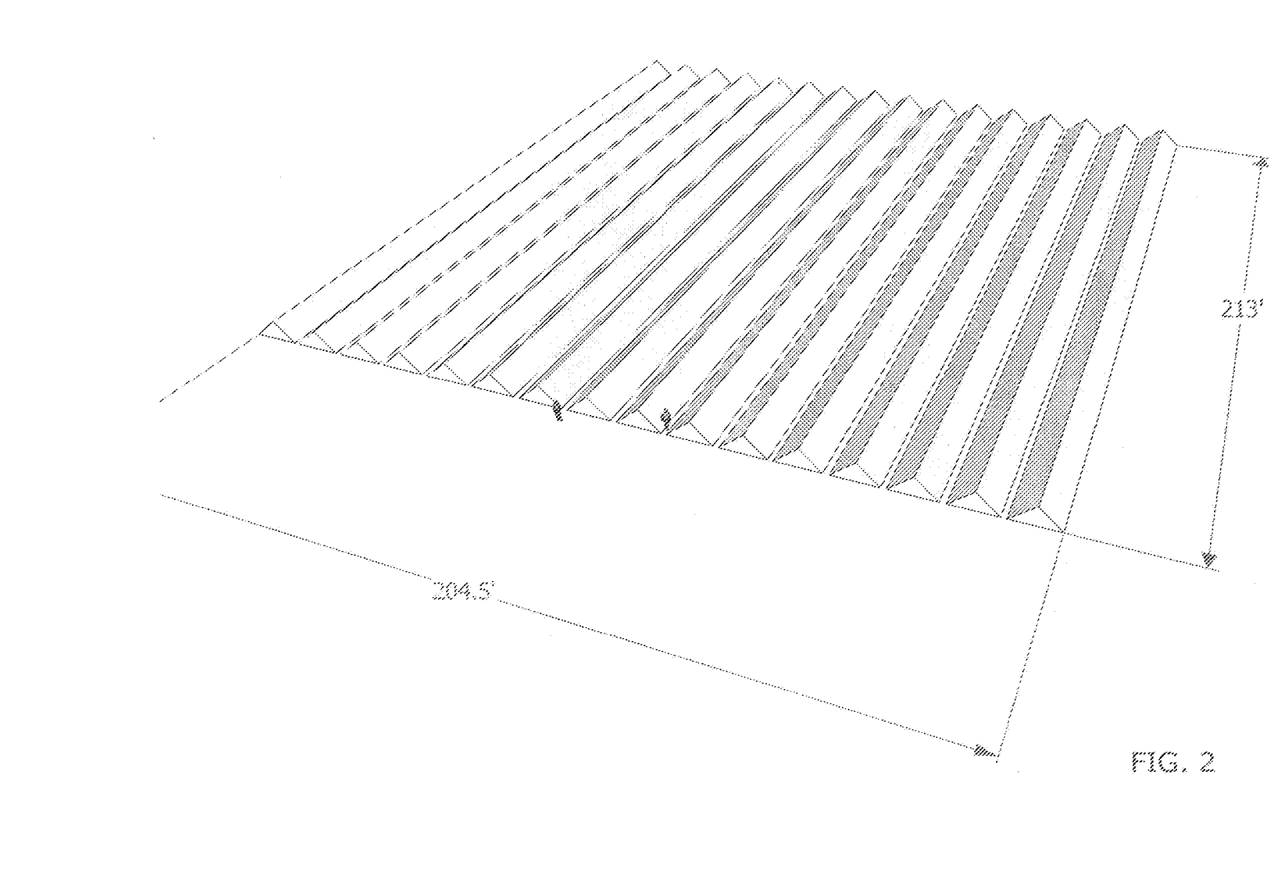
FIG. 2 depicts a scaled representation of a 1 acre layout containing 16 photo-bioreactors.
Figure 4:
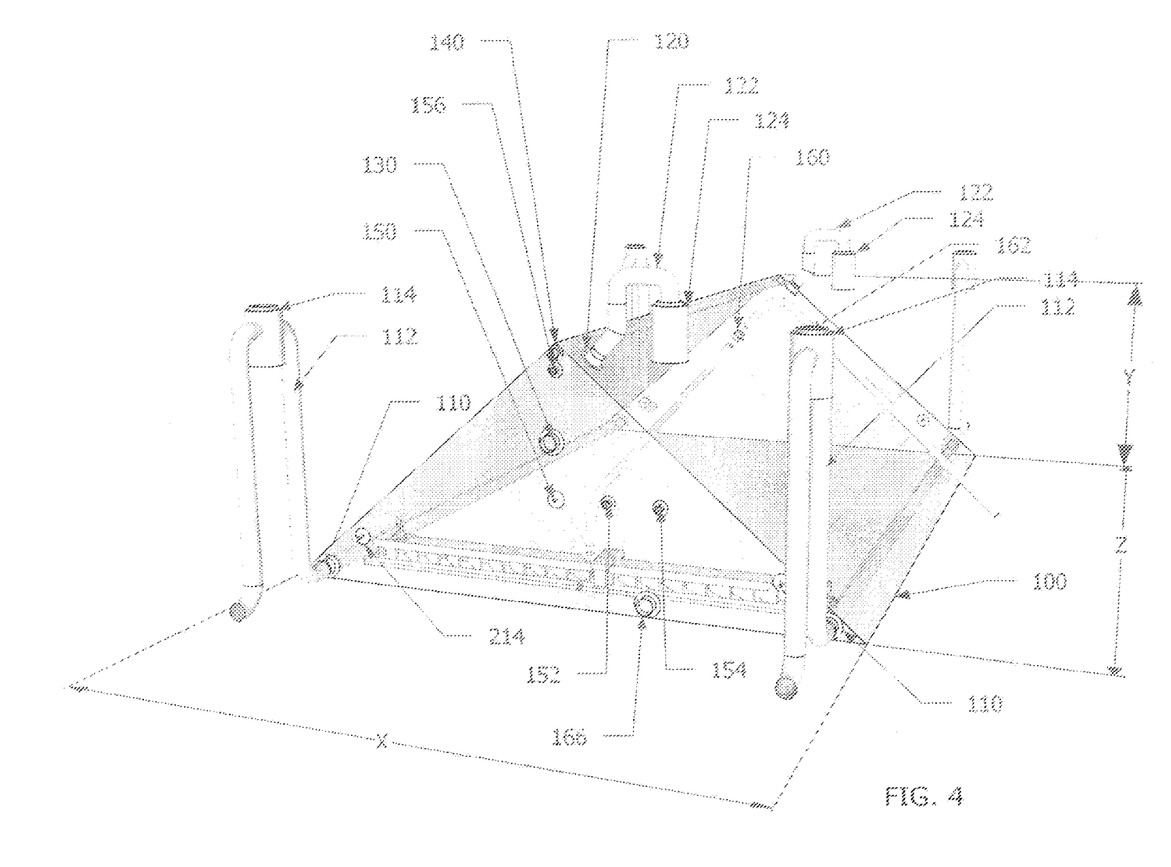
FIG. 4 depicts the front view of a growth chamber and its inner components according to an embodiment of the present invention.

As depicted in FIG. 1, a component 100, according to an embodiment of the present invention, is a transparent, heat weld-able plastic material, 5-20 mils thick, and heat welded along the perimeter to make it a fully enclosed pyramid shape growth chamber. The material of construction can be a film composed of LDPE, PHA, KYNAR or any other composite film that is heat weld-able. In this example embodiment, the dimensions of the growth chamber, as depicted in FIG. 4, can be as follows: X could be between 4 ft to 16 ft, Y could be between 2 ft to 8 ft, and Z could be between 4 ft to 400 ft. In certain embodiments, the component 100 can comprise a plurality of elongated panels connected edgewise to define a tubular configuration, wherein two end panels seal the ends of the bioreactor. In certain aspects, the elongated panels can be arranged such that the tubular configuration comprises a generally triangular configuration.

Figure 9A:
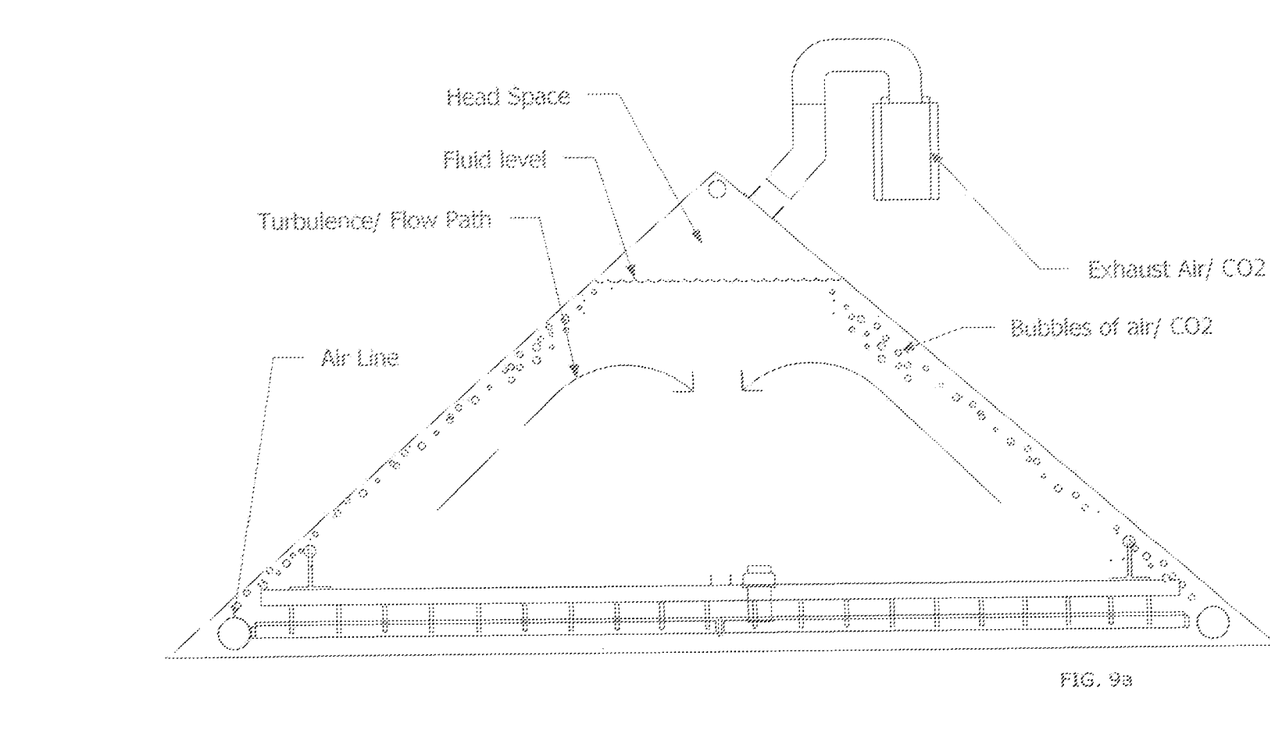
FIG. 9a depicts the front view of the current embodiment in which the turbulent flow path can be seen, as well as the overall fluid level of the culture.
Figure 9B:
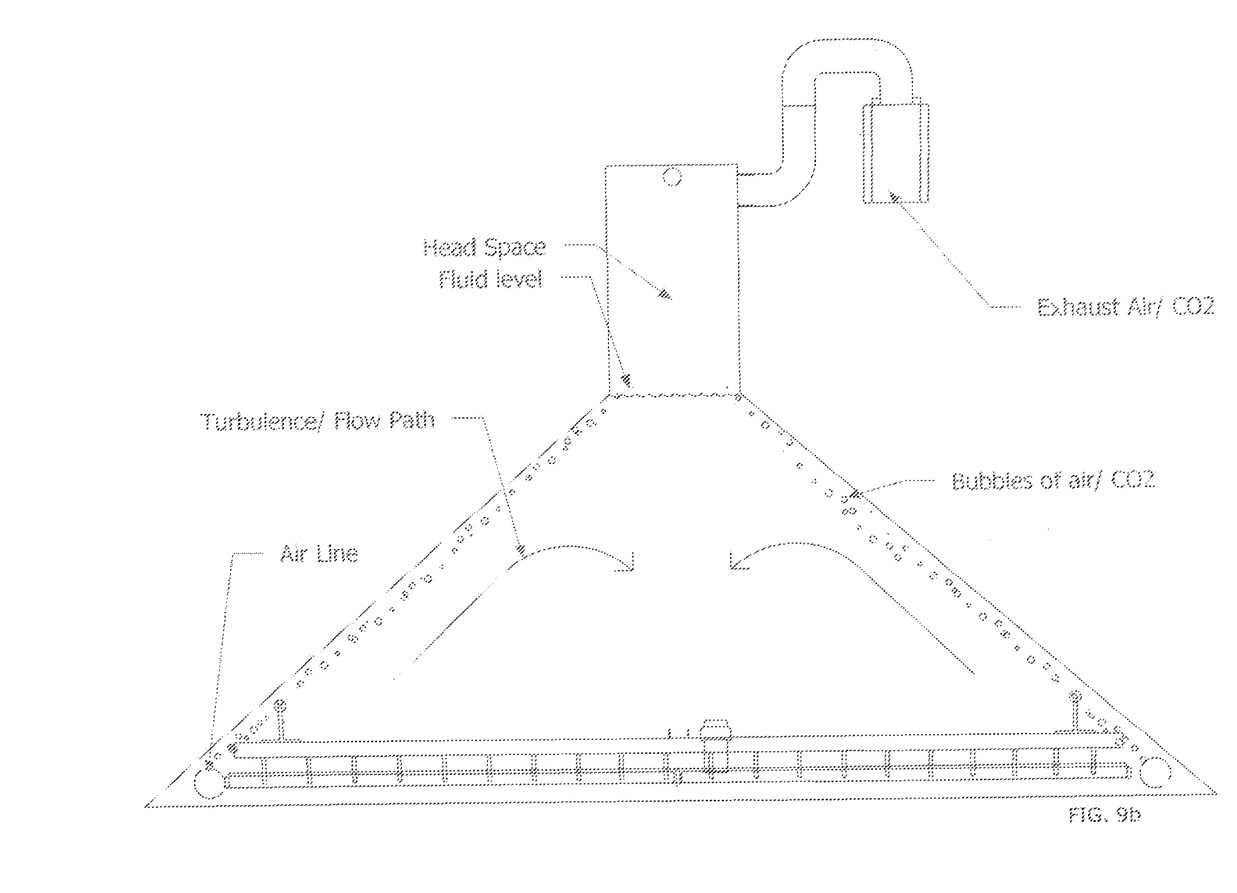
FIG. 9b depicts the front view of another possible embodiment and related chamber geometry, in which the turbulent flow path can be seen, as well as the overall fluid level of the culture.

As depicted in FIG. 9b, in certain aspects, the component 100 as depicted in FIG. 9b, has a different geometry that increases the headspace above the fluid level, thus increasing the volume of water vapor. This geometry could be applicable for harvest of ethanol vapor through the Exhaust Air/Return CO2 line, as depicted in FIG. 1.

Figure 9C:
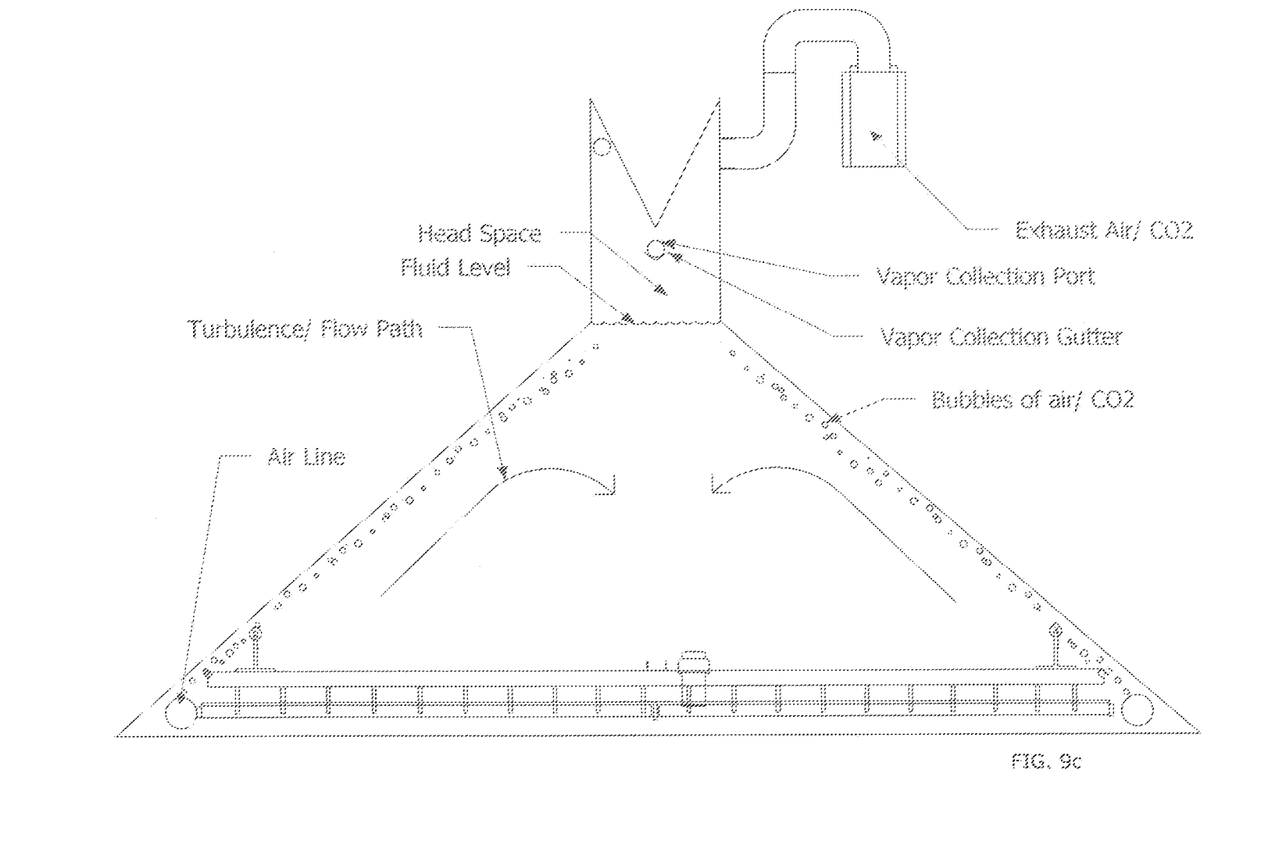
FIG. 9c depicts the front view of yet another possible embodiment and related chamber geometry, in which the turbulent flow path can be seen, as well as the overall fluid level of the culture

As depicted in FIG. 9c, in certain aspects, component 100 as depicted in FIG. 9c, has a different geometry that increases the headspace above the fluid level, and also increases the overall surface area of plastic not in contact with the culture. The increase in headspace in combination with the increase in surface area above the fluid level, allows for more condensation to form on the sides of the reactor. The V-geometry of the upper portion of the reactor, as depicted in FIG. 9c, would cause condensate to develop on the inner wall of the growth chamber within the reactor, and drip down into the vapor collection gutter, which would be built on a slope to cause the condensate to flow towards vapor collection port, and collected for processing. This geometry could be applicable for harvest of ethanol vapor through the vapor collection port as depicted in FIG. 9c.

Figure 3:
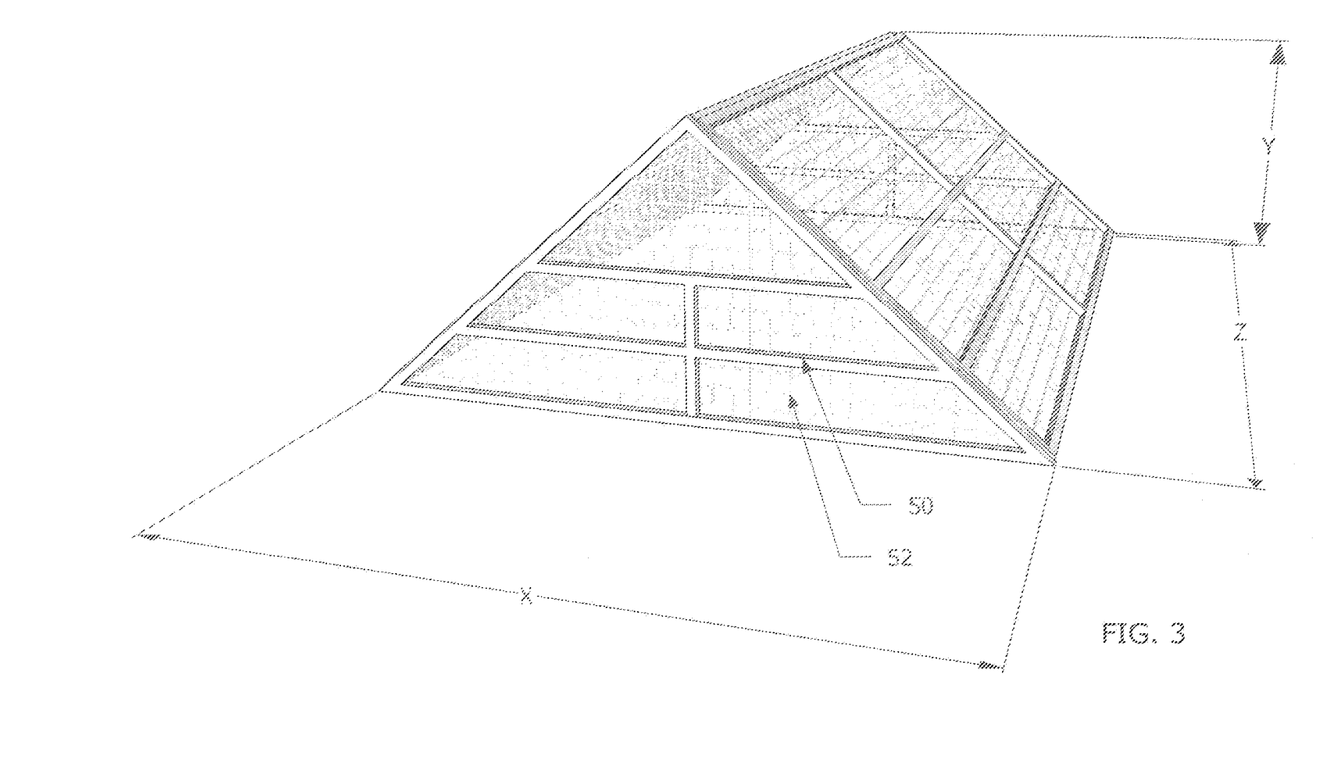
FIG. 3 depicts a support structure for a photo-bioreactor chamber according to an embodiment of the present invention.

As depicted in FIG. 3, the support structure provides a pyramidal geometry allowing sunlight to penetrate into the reactor. In certain aspects, component 50 can comprise a steel beam of 2 in×2 in cross section, such as UNISTRUT steel beam, and is connected at intersections via steel weld, or UNISTRUT fittings. As depicted in FIG. 3, component 52 can be a steel cage, cut to fit appropriate dimensions. The cell size of the cage (component 52) can be range in size from 2 in×2 in to 6 in×6 in.

Components 110, 120, 130, 140, 150, 152, 154, 156, 160, 166 and 214 are plastic fittings that can be flanged, and have various sizes, and terminal ends. Components 110, 120, 130, 140, 150, 152, 154, 156, 160, 166 and 214 are connected to component 100 via heat weld. Materials other than plastic or steel, such as aluminum, that are sturdy and strong can also be used in any of the various embodiment described herein.

1. Intake Air System

According to an embodiment of the present invention, the intake air system consisting of components 110-118, also includes an air-blower, piping, control valves, filtration, and an air sparger found within the chamber.

Component 114 is an intake air filter of pore size of about 0.2 um to 1 um which can be connected to component 112 via a tri-clover connection, silicone gasket, and tri-clover clamp.

Figure 5:
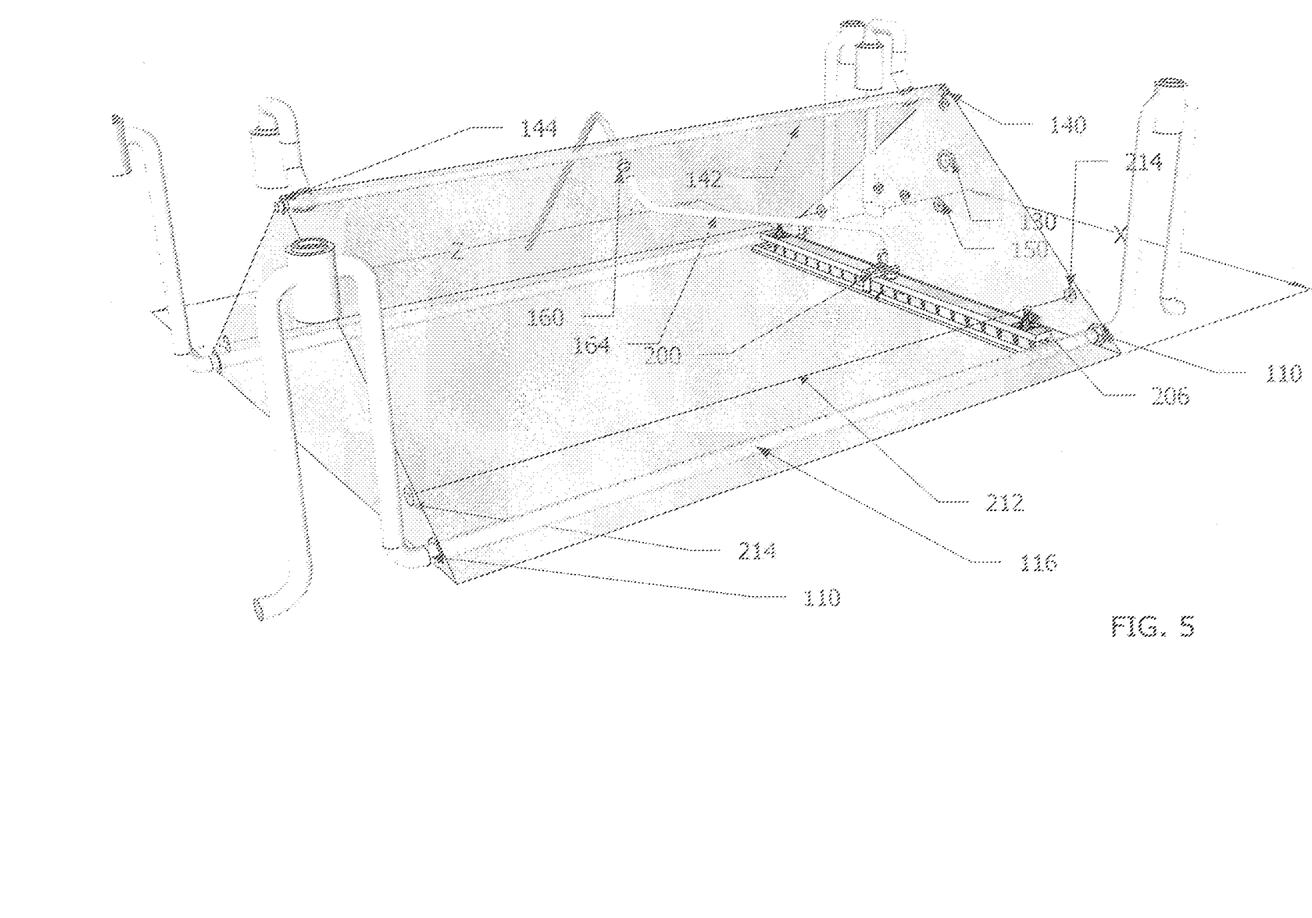
FIG. 5 depicts the back/side view of a growth chamber and its attached inner components according to an embodiment of the present invention.
Figure 6:
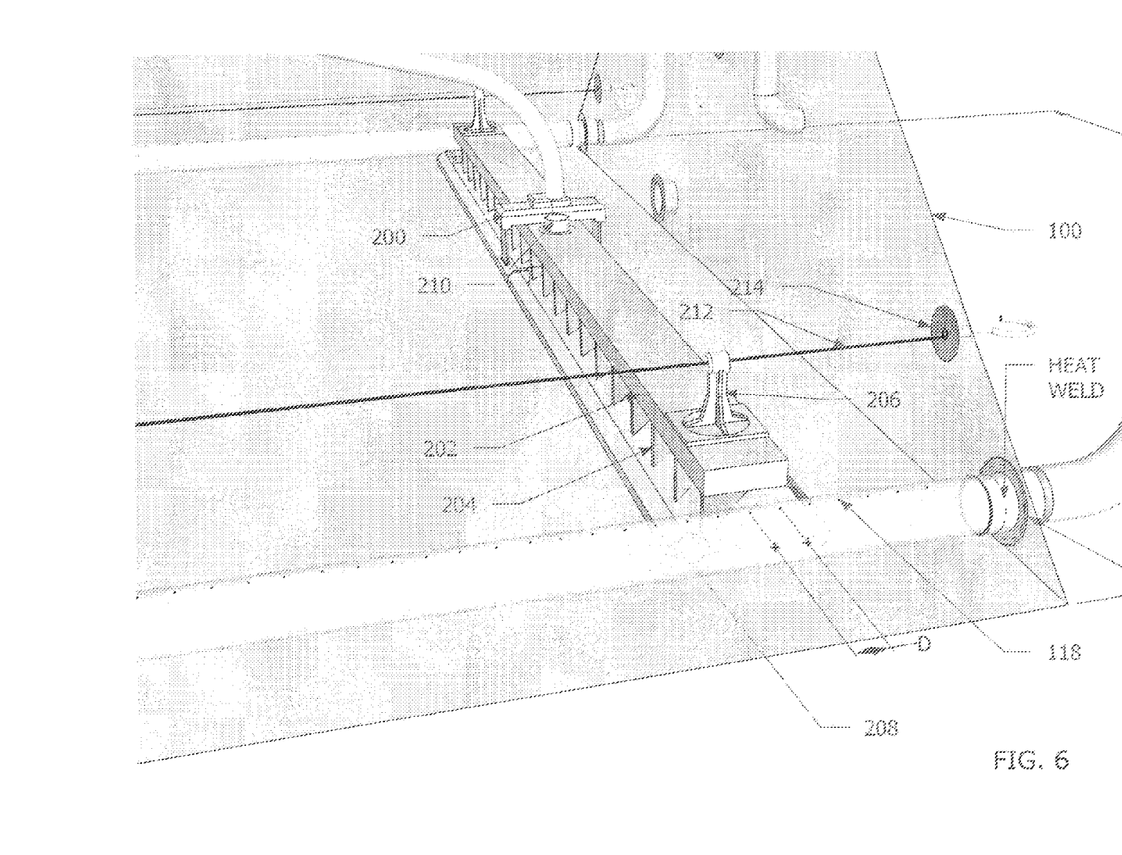
FIG. 6 depicts a close-up view of a harvest apparatus and air sparger line according to an embodiment of the present invention.

Component 112 can be a silicone line of about 2 in to 4 in in diameter with a tri-clover fitting at both of its terminals, and connected to component 110, via a tri-clover connection, silicone gasket, and tri-clover clamp. Component 110 can be a two sided, flanged, plastic fitting, of about 2 in to 4 in in diameter, with a tri-clover connection on the exterior end, and a cylindrical sleeve on the interior end. Component 110 connects to component 100 via heat-weld, producing a port from the exterior side of the growth chamber to the interior. On the interior side, component 110 can be connected to component 116 via heat weld, as depicted in FIG. 6, and represented by a dashed line. As depicted in FIG. 5, component 116 is the air sparger found within the growth chamber, and can be composed of transparent (or translucent), heat weld-able plastic material (or Plexiglas or glass), 5-20 mils thick, and heat welded along the perimeter to make it a fully enclosed tube. As depicted in FIGS. 5 and 6, component 116 can be perforated along its length. As depicted in FIG. 6, the distance between each orifice can range from about 2 in to 24 in, represented by distance D, and the diameter of each orifice (component 118) can be about 1/64 in to 1/4 in.

As depicted in FIG. 5, component 116 runs the length of the growth chamber and reconnects via heat weld to component 110 found on the opposite end of the growth chamber. Component 110 can be a two sided, flanged, plastic fitting with a tri-clover connection on the exterior end, and a cylindrical sleeve on the interior end. Component 110, again, connects with component 112 via a tri-clover connection, silicone gasket, and tri-clover clamp. Component 112 can be a silicone line of 2 in to 4 in in diameter with a tri-clover fitting at both of its terminals, and can connect to component 114 via a tri-clover connection, silicone gasket, and tri-clover clamp.

2. Exhaust Air/Return $CO_2$

According to an embodiment of the present invention, the exhaust air/return CO2 system consists of components 120-124, and allows for the exhaust of intake air. Other than the components directly attached to the growth chamber, the system also contains additional plumbing, filtration, control valves, and instrumentation to accomplish several jobs As depicted in FIG. 4, component 120, which can be a flanged, plastic tri-clover fitting of diameter of about 1 in to 4 in, is connected to component 100 via heat weld. Component 120 is then connected to component 122 via a tri-clover connection, silicone gasket, and tri-clover clamp. Component 122 can be a silicone line of about 1 in to 4 in in diameter with a tri-clover fitting at both of its terminals, and connected to component 124, via a tri-clover connection, silicone gasket, and tri-clover clamp. Component 124 can be an exhaust air filter of pore size 0.2 um to 1 um. The air, and/or, CO2 mixture being purged through the exhaust filter has the option of returning back to the blower if CO2 is detected in the growth chamber, or to be purged into the atmosphere if no CO2 has been detected.

3. Water Delivery

According to an embodiment of the present invention, the water delivery system consists of additional plumbing and infrastructure such as control valves, CIP plumbing, and flow meters, and allows for controlled delivery of medium into the growth chamber. Component 130 can be used as the method of supplying an aqueous solution to the apparatus.

Component 130, as depicted in FIG. 4, can be a flanged, plastic tri-clover fitting of diameter of about 1 in to 4 in and is connected to component 100 via heat weld. Additional plumbing, for seawater, or fresh water can be connected to component 130 via a tri-clover connection, silicone gasket, and tri-clover clamp. Component 130 can also be used as an entry point for CIP through system plumbing.

4. Nutrient Delivery

According to an embodiment of the present invention, the nutrient delivery system, consisting of components 140-144, allows for even distribution of nutrient throughout the entire length of the reactor, thus eliminating uneven concentrations of nutrient within the system. The system consists of additional plumbing and infrastructure such as control valves, CIP plumbing, and flow meters, and allows for controlled delivery of nutrient into the growth chamber.

Figure 7:
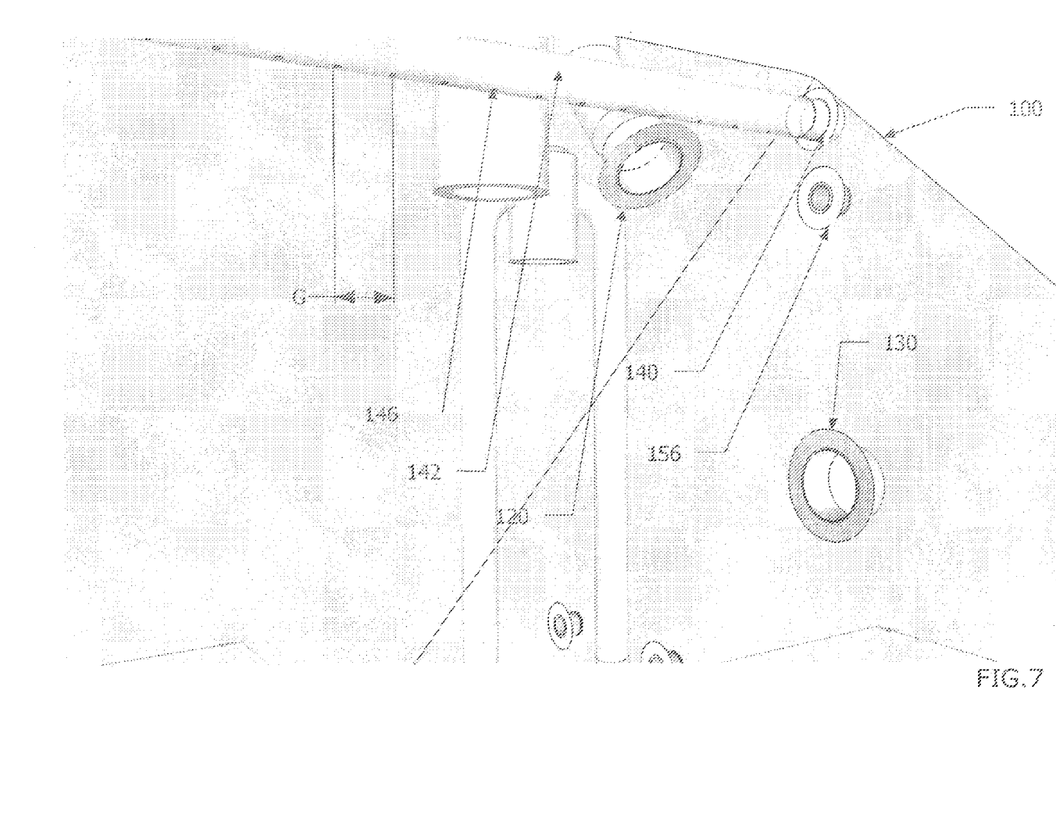
FIG. 7 depicts a close-up view of a nutrient delivery line according to an embodiment of the present invention.

Component 140, as depicted in FIG. 4 and FIG. 7, can be a two sided, flanged, plastic fitting with diameter of about 1 in to 4 in, with a tri-clover connection on the exterior end, and a cylindrical sleeve on the interior end, and can be connected to component 100 via heat weld.

On the interior side, component 140 can be connected to component 142 via heat weld, as depicted in FIG. 7. Component 142 is perforated nutrient delivery tube found within the growth chamber, and can be composed of transparent, heat weld-able plastic material, about 5-20 mils thick, and heat welded along the perimeter to make it a fully enclosed tube. Component 142 can be attached to component 100 via heat weld along its entire length. As depicted in FIGS. 5 and 7, Component 142 can be perforated along its entire length. As depicted in FIG. 7, the distance between each orifice is represented by letter G, and can range from about 2 in-24 in. As depicted in FIG. 7, the diameter of each orifice can be about 1/64 in-1/4 in.

As depicted in FIG. 5, at the opposite side of the growth chamber, component 142 connects to, component 144 via heat weld. Component 144, as depicted in FIG. 5, can be a flanged plastic fitting with a cylindrical sleeve of diameter of about 1 in to 4 in, facing the interior of the growth chamber, but having no through opening. In another embodiment, component 144 can be a two sided, flanged, plastic fitting with diameter of about 1 in –4 in, with a tri-clover connection on the exterior end, and a cylindrical sleeve on the interior end, and capped on the exterior end to prevent flow through.

5. Control Instrumentation

According to an embodiment of the present invention, the control Instrumentation, which contains components 150-156, consists of instrumentation that is configured for delivering data such as temperature, pH, and CO2 levels within the chamber. An ability to ascetically sample from the reactor is also built into this system. The instrumentation is an integral part of being able to control and measure the levels of CO2 being delivered into the system, thus maintaining optimal growth, and using up to 90% of the CO2 without wasting this important ingredient. All information is routed through the control box.

Component 150, as depicted in FIG. 4, can be a flanged plastic fitting with a hose barb of 1/4 in to 1 in in diameter, and connected to component 100 via heat weld. Additional assemblies can be added to the hose barb, such as 1 ft 4 in to 1 in ID silicone tubing with a clamp, and a plug. This assembly, beginning with component 150, comprises the sampling port of the growth chamber, and can be used for as an alternative port for additions and inoculations.

Component 152, as depicted in FIG. 4, can be a flanged, plastic tri-clover fitting of diameter of 3/4 in to 4 in, and is connected to component 100 via heat weld. Component 152 allows for insertion of instrumentation such as a temperature probe, pH probe, or oxygen sensor. The instrumentation can be adapted to fit a tri-clover fitting, and connect to component 152 via a tri-clover connection, silicone gasket, and tri-clover clamp.

Component 154, as depicted in FIG. 4, can be a flanged, plastic tri-clover fitting of diameter of 3/4 in to 4 in, and is connected to component 100 via heat weld. Component 154 allows for insertion of instrumentation such as a temperature probe, pH probe, or oxygen sensor. The instrumentation can be adapted to fit a tri-clover fitting, and connect to component 154 via a tri-clover connection, silicone gasket, and tri-clover clamp.

Component 156, as depicted in FIG. 4, can be a flanged, plastic tri-clover fitting of diameter of ¾ in to 4 in, and is connected to component 100 via heat weld. Component 156 allows for insertion of instrumentation such as a CO2 sensor. The instrumentation can be adapted to fit a tri-clover fitting, and connect to component 156 via a tri-clover connection, silicone gasket, and tri-clover clamp.

Figure 10:
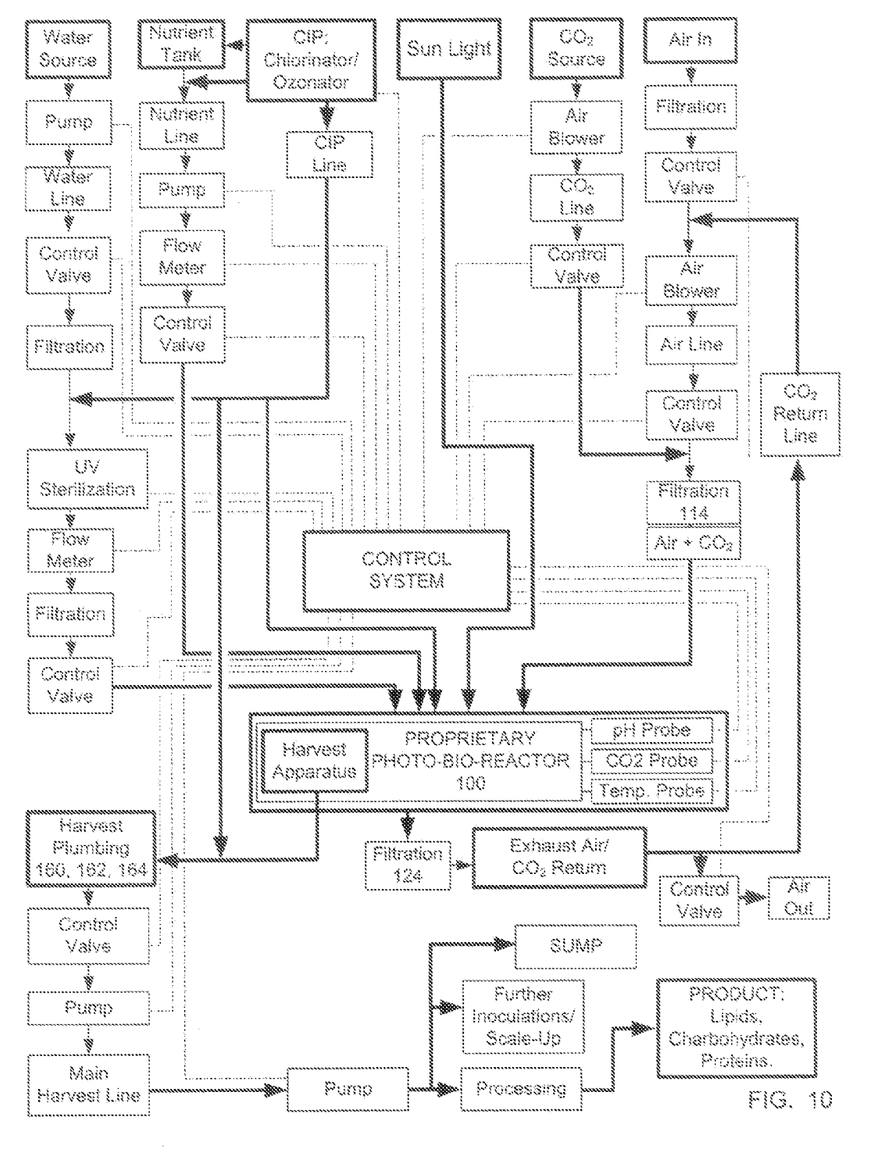
FIG. 10 depicts a flow diagram of the process in relation to the novel photo-bioreactor. The dashed lines in the FIG. 10 represent electrical connections of said components to the control system and elucidate the remote control abilities of the system.

Instrumentation connected to the growth chamber, can be connected to the control box as depicted in FIG. 1, and used to relay data to the control center. Electrical connections of instruments to control box are depicted in FIG. 10.

6. Control Instrumentation

According to an embodiment of the present invention, the harvest plumbing sub-assembly, consisting of components 160-166, connects the harvest apparatus to a harvest pump and further harvest and CIP infrastructure such as plumbing and control valves. The harvest plumbing facilitates the removal of concentrated biomass from the photo-bioreactor via specialized harvest apparatus.

Component 160, as depicted in FIG. 4 and FIG. 5, can be a two sided, flanged, plastic fitting, 1 in to 4 in in diameter, with a tri-clover connection on both the exterior end, and the interior end. Component 160 is connected to component 100 via heat weld. On the exterior side of the growth chamber, as depicted in FIG. 4, component 160 is connected to component 162, via a tri-clover connection, silicone gasket, and tri-clover clamp. Component 162 can be a silicone line of 1 in to 4 in in diameter with a tri-clover fitting at both of its terminals, and can be connected to a pump and additional CIP/harvest plumbing and valve work.

On the interior side of the chamber, component 160, as depicted in FIG. 5, can be connected to component 164 via a tri-clover connection, silicone gasket, and tri-clover clamp. Component 164, as depicted in FIG. 5, can be a silicone line of 1 in to 4 in in diameter, with a tri-clover fitting at both of its terminals, and can be connected to the harvest apparatus' inlet port, which is component 210, via a tri-clover connection, silicone gasket, and tri-clover clamp.

Component 166, as depicted in FIG. 4, is an additional port designated for harvest of the entire volume of culture within the culture chamber. Component 166, can be a flanged plastic fitting with a tri-clover terminal of 1 in to 4 in in diameter, and connected to component 100 via heat weld. Component 166 can connect directly to harvest plumbing as depicted in FIG. 1.

7. Harvest Apparatus

In this example embodiment, the harvest apparatus, which consists of components 200-214, allows for efficient removal of concentrated biomass, thus saving on the amount of water needed to produce biomass. The apparatus also reduces time spent harvesting biomass from the reactor, by reducing reactor re-fill times and a de-wetting of biomass.

Figure 8:
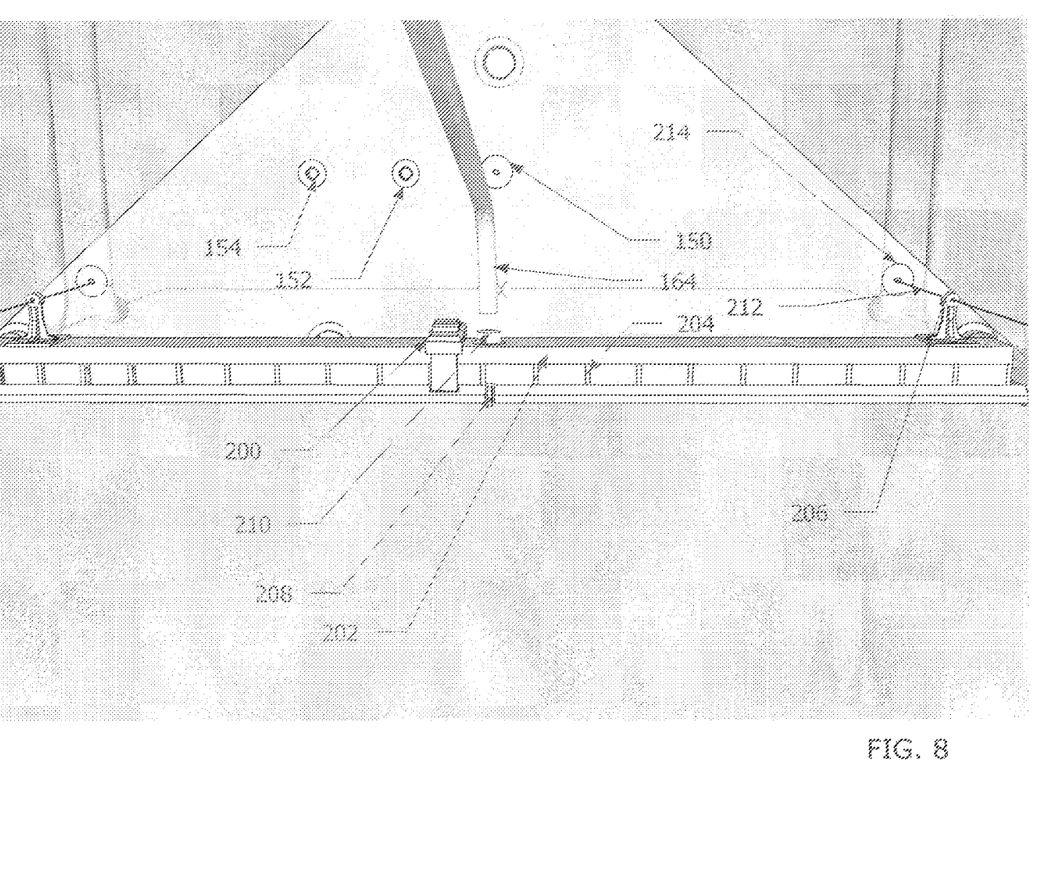
FIG. 8 depicts a view from inside a growth chamber of a harvest apparatus.

Component 200, as depicted in FIGS. 5, 6 and 8, is a driving mechanism for the harvest apparatus. Component 200 can contain a motor, which drives the entire harvest apparatus forwards and backwards. Component 200 can also be driven by the suction force being created across a mechanism, which creates torque, which can be transferred to the wheels of the apparatus (components 208) and thus drive the harvest apparatus forwards and backwards. Component 200 rests on top of the harvest apparatus, and can be connected to component 202 via clip in mechanism, plastic screws, or heat weld.

As depicted in FIG. 6, component 210 can be a flanged, plastic tri-clover fitting with diameter of 1 in to 4 in and can be attached to component 202 via heat weld. Component 210 serves as the connection point between the harvest apparatus, and the harvest plumbing, which is comprised of components 160-164, and can be connected to the harvest plumbing (component 164), via a tri-clover connection, silicone gasket, and tri-clover clamp. Component 210 allows for the transfer of suction pressure created by a harvest pump, through the harvest pump, and across a manifold chamber signified by component 202.

Component 202, as depicted in FIG. 8, is a hollow, plastic chamber, which makes up the top portion of the suction manifold of the harvest apparatus, and distributes the suction pressure across its length and into the components 204 (20 total as depicted in FIG. 8). Components 204, can be made of plastic material, and are narrow, hollow fingers, which are design to collect settled biomass from the growth chamber floor via suction pressure created by the harvest pump.

Component 206, as depicted in FIGS. 6 and 8, is plastic guidepost, which can be made of plastic material, and be connected to component 202 via heat weld. Component 206 contains an eyelet through which component 212 passes. Component 212 is a guide cable, which can be coated with a plastic material, and is connected on either end of the growth chamber to component 214 via heat weld. Component 214, as depicted in FIG. 6, can be a flanged fitting that contains a hooking device on the exterior side of the growth chamber, thus allowing one to fasten the ends of component 214, and apply tension to the guide cables (components 212), hence creating two taunt guide lines running the length of the growth chamber to guide the harvest apparatus.

According to an embodiment of the present invention, a smaller harvest pump can be located inside the growth chamber, directly above component 210, such that the suction force is applied directly through the port 210, and into the collection manifold 202.

In an example embodiment of the present invention, the contributing subassemblies to the primary growth chamber comprise the intake air system consisting of components 110-116; Exhaust Air/CO2 Return, which consists of components 120-124; water delivery which consists of component 130; Nutrient delivery, which consists of components 140-144; Control Instrumentation which contains components 150-156; Harvest plumbing, consisting of components 160-166; and Harvest apparatus, which consists of components 200-214.

The intake air system, consisting of components 110-116 in this example embodiment, also includes an air-blower, piping, control valves, filtration, and an air sparger found within the chamber. These parts allow for clean delivery of air into the growth chamber thus providing sufficient turbulence within the growth chamber, which results in an increase in circulation, and develops a turnover rate that increases cellular exposure to sunlight (or artificial light). A cross sectional front view of the reactor that depicts the turbulent flow path caused by the aeration system can be seen in FIG. 9a. This aeration of culture also results in an essential de-oxygenation of the microbial culture, thus increasing overall productivity.

Another key characteristic of the air system, of this example embodiment, in relation to the geometry of the photo-bioreactor is the path that the curtain of air is forced to take along the inner surface of the reactor, as seen in FIG. 9a.

This path allows for the scouring of the inner surface by the small air bubbles, which in turn eliminate the accumulation of bio-film.

The intake air may be coupled with a CO2 source, which may be injected into the intake air-system just prior to the intake filter, and therefore mixed with the culture as it is bubbled through the air sparger. This allows for the CO2 to become diffuse into the culture, and take the form of carbonic acid. In this manner, the CO2 becomes available for utilization by the photosynthetic microbes The Exhaust Air/Return CO2 system consists of components 120-124 in this example embodiment and allows for the exhaust of intake air. Other than the components directly attached to the growth chamber, the system also contains additional plumbing, filtration, control valves, and instrumentation to accomplish several tasks. The first is to cleanly exhaust the intake air without compromising sanitation of the culture within the chamber. The second allows for a return loop to remediate any un-used CO2, and return it back into the growth chamber. The return loop feature of the apparatus also allows one to capture any valuable products being vaporized by culture within the growth chamber, such as ethanol for example.

The water delivery system, of this example embodiment, consists of additional plumbing and infrastructure such as control valves, CIP plumbing, and flow-meters, and allows for controlled delivery of medium into the growth chamber. Component 130 may be used as the entry point for water delivery into the growth chamber.

The nutrient delivery system, of this example embodiment, consisting of components 140-144 and allows for even distribution of nutrient throughout the entire length of the reactor, thus eliminating uneven concentrations of nutrient within the system. The system consists of additional plumbing and infrastructure such as control valves, CIP plumbing, and flow meters, and allows for controlled delivery of nutrient into the growth chamber.

The control Instrumentation, of this example embodiment, which contains components 150-156, consists of instrumentation that is configured for delivering data such as temperature, pH, and CO2 levels within the chamber. An ability to ascetically sample from the reactor is also built into this system. The injected into the intake air-system just prior to the intake filter and therefore mixed with the culture as it is bubbled through the air sparger. This allows for the CO2 to become diffuse into the culture, and take the form of carbonic acid. In this manner, the CO2 becomes available for utilization by the photosynthetic microbes The Exhaust Air/Return CO2 system consists of components 120-124 in this example embodiment and allows for the exhaust of intake air. Other than the components directly attached to the growth chamber, the system also contains additional plumbing, filtration, control valves, and instrumentation to accomplish several tasks. The first is to cleanly exhaust the intake air without compromising sanitation of the culture within the chamber. The second allows for a return loop to remediate any un-used CO2, and return it back into the growth chamber. The return loop feature of the apparatus also allows one to capture any valuable products being vaporized by culture within the growth chamber, such as ethanol for example.

The water delivery system, of this example embodiment, consists of additional plumbing and infrastructure such as control valves, CIP plumbing, and flow-meters, and allows for controlled delivery of medium into the growth chamber. Component 130 may be used as the entry point for water delivery into the growth chamber.

The nutrient delivery system, of this example embodiment, consisting of components 140-144 and allows for even distribution of nutrient throughout the entire length of the reactor, thus eliminating uneven concentrations of nutrient within the system. The system consists of additional plumbing and infrastructure such as control valves, CIP plumbing, and flow meters, and allows for controlled delivery of nutrient into the growth chamber.

The control Instrumentation, of this example embodiment, which contains components 150-156, consists of instrumentation that is configured for delivering data such as temperature, pH, and CO2 levels within the chamber. An ability to ascetically sample from the reactor is also built into this system. The instrumentation is an integral part of being able to control and measure the levels of CO2 being delivered into the system, thus maintaining optimal growth while using the CO2 without wasting this important ingredient. All information is routed through the control box.

The harvest plumbing, of this example embodiment, consisting of components 160-166 and connects the harvest apparatus to a harvest pump and further harvest and CIP infrastructure such as plumbing and control valves. The harvest plumbing facilitates the removal of concentrated biomass from the photo-bioreactor via a specialized harvest apparatus.

The harvest apparatus, of this example embodiment, which consists of components 200-214, allows for efficient removal of concentrated biomass, thus saving on the amount of water needed to produce biomass. The apparatus also reduces time spent harvesting biomass from the reactor, by reducing reactor re-fill times, a de-wetting of biomass.

The following patents and publications are incorporated herein by reference in their entirety: U.S. Publication number 2011/0104790; and U.S. Pat. Nos. 7,770,322 and 5,541,056.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. A photo-bioreactor system for producing biomass comprising
   a) a tubular growth chamber comprising:
      i) a plurality of elongated transparent panels arranged edgewise, wherein at least two angled sides of the panels intersect at an apex;
      ii) a generally flat bottom; and
      iii) two end panels affixed to the plurality of elongated transparent panels to enclose the tubular growth chamber;
   b) at least one guide wire extending between the two end panels;
   c) a harvest manifold engaged to the guide wire and movable along the flat bottom of the tubular growth chamber, the harvest manifold comprising a plurality of hollow fingers, wherein a vacuum is drawn through the hollow fingers; and
   d) a vacuum pump, wherein the vacuum draws the biomass into the harvest manifold.

2. The photo-bioreactor system of claim 1, wherein the system lacks a cooling system.

3. The photo-bioreactor system of claim 1 further comprising sampling instrumentation that measures conditions within the tubular growth chamber.

4. The photo-bioreactor system of claim 1 further comprising a nutrient delivery system.

5. The photo-bioreactor system of claim 4, wherein the nutrient delivery system comprises at least one nutrient delivery tube.

6. The photo-bioreactor system of claim 5, wherein the nutrient delivery tube is proximate to the apex of the tubular growth chamber.

7. The photo-bioreactor system of claim 4, wherein the nutrient delivery system provides even distribution of nutrient throughout the entire length of the photo-bioreactor.

8. The photo-bioreactor system of claim 1 further comprising a support structure comprising a plurality of intersecting beams.

9. The photo-bioreactor system of claim 1 further comprising an exhaust assembly operably linked to the tubular growth chamber proximate to the apex.

10. The photo-bioreactor system of claim 9, wherein the exhaust assembly comprises an exhaust filter.

11. A photo-bioreactor system for producing biomass comprising
   a) a tubular growth chamber comprising:
      i) a plurality of elongated transparent panels arranged edgewise, wherein at least two angled sides of the panels intersect at an apex;
      ii) a generally flat bottom; and
      iii) two end panels affixed to the plurality of elongated transparent panels to enclose the tubular growth chamber;
   b) at least one guide wire extending between the two end panels;
   c) a harvest manifold engaged to the guide wire and movable along the flat bottom of the tubular growth chamber, the harvest manifold comprising a plurality of hollow fingers, wherein a vacuum is drawn through the hollow fingers; and
   d) at least one air sparger extending along the intersection of one of the sides and the bottom.

12. The photo-bioreactor system of claim 11, wherein the air sparger comprises a plurality of perforations that expel air into the tubular growth chamber.

13. The photo-bioreactor system of claim 12, wherein the perforations are oriented to Previously Presented air against the angled sides of the tubular growth chamber.

14. A method of producing a biomass comprising mixing a microbial culture of photosynthetic organisms and a nutrient solution in a photo-bioreactor system of claim 1.

15. The method of claim 14 further comprising drawing a biomass into the harvest manifold.

16. The method of claim 15 further comprising collecting the biomass via the harvest manifold.

17. The method of claim 15 further comprising a) measuring carbon dioxide levels in the photo-bioreactor system; and b) optionally, increasing air delivered to the photo-bioreactor system if the carbon dioxide falls beneath a predetermined threshold.

* * * * *